(12) United States Patent
Fomina (10) Patent No.: US 8,664,251 B1
(45) Date of Patent: Mar. 4, 2014

(54) RYANODINE RECEPTOR INHIBITORS FOR TREATMENT OF T-CELL MEDIATED DISORDERS

(75) Inventor: Alla F. Fomina, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 497 days.

(21) Appl. No.: 12/727,865

(22) Filed: Mar. 19, 2010

Related U.S. Application Data (63) Continuation-in-part of application No. 12/714,198, filed on Feb. 26, 2010, now abandoned.

(60) Provisional application No. 61/208,861, filed on Feb. 26, 2009.

(51) Int. Cl.
  *A01N 43/50* (2006.01)
  *A61K 31/415* (2006.01)
  *A01N 43/08* (2006.01)
  *A61K 31/34* (2006.01)

(52) U.S. Cl.
  USPC .......................................... 514/390; 514/461

(58) Field of Classification Search
  None
  See application file for complete search history.

(56) References Cited

U.S. PATENT DOCUMENTS

| | | | | |
|---|---|---|---|---|
| 2001/0053790 | A1* | 12/2001 | Mangat et al. | 514/390 |
| 2004/0242646 | A1* | 12/2004 | Anderson et al. | 514/341 |
| 2011/0281750 | A1* | 11/2011 | Corvol et al. | 506/9 |

OTHER PUBLICATIONS

Chou et al. Journal of Pain and Symptom Management 28 (2004) 2, p. 140-175.*
Gold et al. Journal of Neuroscience Research 77 (2004) 367-377.*
Dolmetsch, R., et al., "Differential activation of transcriptional factors induced by $Ca^{2+}$ response amplitude and duration," *Nature*, vol. 386(6627), pp. 855-858 (Apr. 1997).
Dolmetsch, R., et al., "Calcium oscillations increase the efficiency and specificity of gene expression," *Nature*, vol. 392(6679), pp. 933-936 (Apr. 1998).
Dupuis, G., et al,. "Lectin Interactions with the Jurkat Leukemic T-Cell Line: Quantitative Binding Studies and Interleukin-2 Production," *Journal of Leukocyte Biology*, vol. 43(3), pp. 238-247 (1988).
Feske, S., "Calcium signaling in lymphocyte activation and disease," *Nat. Rev. Immunol.*, vol. 7(9), pp. 690-702 (2007).
Gasser, A., et al., "Activation of T Cell Calcium Influx by the Second Messenger ADP-ribose," *The Journal of Biological Chemistry*, vol. 281(5), pp. 2489-2496 (2006).
Guse, A., et al., "Regulation of calcium signaling in T lymphocytes by the second messenger cyclic ADP-ribose," *Nature*, vol. 398(6722), pp. 70-73 (1999).
Gwack, Y., et al,. "Signalling to transcription: Store-operated $Ca^{2+}$ entry and NFAT activation in lymphocytes," *Cell Calcium*, vol. 42(2), pp. 145-156 (2007).

Hakamata, Y., et al., "Involvement of the brain type of ryanodine receptor in T-cell proliferation," *FEBS Letters*, vol. 352, pp. 206-210 (1994).
Krause, T., et al., "Dantrolene—A review of its pharmacology, therapeutic use and new developments," *Anaesthesia*, vol. 59(4), pp. 364-373 (2004).
Lewis, R., "Calcium Signaling Mechanisms in T Lymphocytes," *Annu. Rev. Immunol.*, vol. 19, pp. 497-521 (2001).
Negulescu, P., et al., "Intracellular calcium dependence of gene expression in single T lymphocytes," *Proc. Natl. Acad. Sci. USA*, vol. 91, pp. 2873-2877 (Mar. 1994).
Putney, J., "A Model for Receptor-Regulated Calcium Entry," *Cell Calcium*, vol. 7(1), pp. 1-12 (1986).
Putney, J., et al., "Capacitative calcium entry channels," *BioEssays*, vol. 21(1), pp. 38-46 (1999).
Schwarzmann, N., et al., "Knock-down of the Type 3 Ryanodine Receptor Impairs Sustained Ca2+ Signaling via the T Cell Receptor/CD3 Complex," *The Journal of Biological Chemistry*, vol. 277(52), pp. 50636-50642 (2002).
Zhao, F., et al., "Dantrolene Inhibition of Ryanodine Receptor Ca2+ Release Channels," *The Journal of Biological Chemistry*, vol. 276(17), pp. 13810-13816 (2001).
Abbruzzese, G., "The medical management of spasticity," *European J. of Neurology*, 2002, 9 (Suppl.1):30-34.
Balantrapu, Swathi, et al., "Perceived Impact of Spasticity is Associated with Spatial and Temporal Parameters of Gait in Multiple Sclerosis," *ISRN Neurology*, vol. 2012, Article ID 675431, pp. 1-6.
Haselkorn, Jodie K., et al., "Overview of Spasticity Management in Multiple Sclerosis. Evidence-Based Management Strategies for Spasticity Treatment in Multiple Sclerosis," *J. of Spinal Cord Medicine*, 2005, vol. 28(2):167-199.
Hosoi, Eiji, et al., "Expression of the Ryanodine Receptor Isoforms in Immune Cells," *J. Immunol*, 2001,167:4887-4894.
Schmidt, R. T., et al., "Comparison of dantrolene sodium and diazepam in the treatment of spasticity," *J. of Neurology, Neurosurgery, and Psychiatry*, 1976, 39:350-356.
Teasell, Robert W., "Managing Advanced Multiple Sclerosis," *Canadian Family Physician*, May 1993, 39:1127-1141.
Knight, Zachary A., "Small Molecule Inhibitors of the PI3-Kinase Family," *Current Topics in Microbiology and Immunology*, 347: 263-278 (2011). Kong, Dexin, et al., "Phosphatidylinositol 3-kinase inhibitors: promising drug candidates for cancer therapy," *Cancer Sci.*, 99(9):1734-1740 (2008).
Matsuda, Satoshi, et al., "Mechanisms of action of cyclosporine," *Immunopharmacology*, 47:119-125 (2000).
Allison, Anthony C., "Immunosuppressive drugs: the first 50 years and a glance forward," *Immunopharmacology*, 47:63-83 (2000).
Barik, S., "Immunophilins: for the love of proteins," *Cell Mol. Life Sci.*, 63:2889-2900 (2006).
Samstag, Yvonne, et al., "Ras initiates phosphatidyl-inositol-3-kinase (PI3K)/PKB mediated signaling pathways in untransformed human peripheral blood T lymphocytes," *Advan. Enzyme Regul.*, 45:52-62 (2005).

(Continued)

*Primary Examiner* — Jeffrey S. Lundgren
*Assistant Examiner* — Michael Schmitt
(74) *Attorney, Agent, or Firm* — Kilpatrick Townsend & Stockton LLP (57) ABSTRACT

This invention relates to methods of treating T-cell mediated diseases or disorders in human or animal subjects, such as autoimmune diseases and chronic graft versus host disease in humans and animals. In particular, the methods comprise administering to the human or animal patient a pharmaceutical composition comprising a ryanodine receptor inhibitor.

15 Claims, 6 Drawing Sheets

(56) References Cited

OTHER PUBLICATIONS

Abraham, Robert T., et al., "Jurkat T cells and development of the T-cell receptor signaling paradigm," *Immunology*, 4:301-308 (2004).
Jager, Heike, et al., "SK2 encodes the apamin-sensitive Ca2+-activated K+ channels in the human leukemic T cell line, Jurkat," *FEBS Letters*, 469:196-202 (2000).
Logsdon, Naomi J., et al., "A Novel Gene, hKCa4, encodes the Calcium-activated Potassium Channel in Human T Lymphocytes," *J. of Biol. Chem.*, 272(52):32723-32726 (1997).
Grissmer, Stephan, et al., "Calcium-activated Potassium Channels in Resting and Activated Human T Lymphocytes," *J. Gen. Physiol.*, 102:601-630 (1993).
Cahalan, Michael D., et al., "The functional network of ion channels in T lymphocytes," *Immunological Reviews*, 231:59-87 (2009).

* cited by examiner

RYANODINE RECEPTOR INHIBITORS FOR TREATMENT OF T-CELL MEDIATED DISORDERS

CROSS-REFERENCES TO RELATED APPLICATIONS

This application is a Continuation-in-Part of U.S. application Ser. No. 12/714,198 filed Feb. 26, 2010 which claims the benefit under 35 U.S.C. §1.119(e) of U.S. provisional Application No. 61/208,861, filed Feb. 26, 2009, the contents of which are incorporated by reference in the entirety.

BACKGROUND OF THE INVENTION

T lymphocytes play a pivotal role in directing the immune responses against foreign pathogens, damaged or transformed cells. However, when deregulated, T cells may mediate a number of pathological diseases such as autoimmune diseases (AD), including type-1 diabetes, rheumatoid arthritis, multiple sclerosis, etc., and may significantly affect the development and progression of inflammatory diseases such as cardiovascular disease and stroke. (Sospedra, M., and Martin, R. (2005) *Annu. Rev. Immunol.* 23(7): 683-747; Menge, T., Weber, M. S., Hemmer, B., Kieseier, B. C., von Budingen, H. C., Warnke, C., Zamvil, S. S., Boster, A., Khan, O., Hartung, H. P., and Stuve, O. (2008) Drugs 68(17): 2445-68; Cope A. P., Schulze-Koops H., and Aringer M. (2007) *Clin Exp Rheumatol.* 25(5 Suppl 46):54-11; Yoon J W, and Jun H S. (2005) *Am J. Ther.* 12(6):580-91; Skapenko A., Leipe J., Lipsky P. E., and Schulze-Koops H. (2005) *Arthritis Res. Ther.* 7(Suppl 2):54-14). The immune system is also responsible for the destruction of organ transplants, the so called graft versus host disease (GVHD) (Jacobsohn D. A., and Vogelsang G. B. (2007) *Orphanet J. Rare Dis.* 4:2:35; Ferrara J. L., Cooke K. R., and Teshima T. (2003) Int. J. Hematol. 78(3):181-7). Currently available therapies for these T cell-mediated diseases are largely unsatisfactory primarily because all the available drugs are either only partially effective in reducing exacerbation and slowing down the disease progression, or produce severe side effects.

Naïve or memory T cells are quiescent cells circulating in the body and are commonly referred to as resting T cells. Resting T cells express T cell receptors (TCR) that recognize a specific antigen on an antigen-presenting cell. In order to participate in immune response, resting T cells undergo process of activation triggered by TCR crosslinking with an antigen (Favero, J. and Lafont, V (1998) *Biochem. Pharmacol.* 56(12): 1539-47; Killeen, N., Irving, B. A., Pippig, S., and Zingler, K. (1998) *Curr. Opin. Immunol.* 10(3): 360-7). During the activation phase, T cells start to express specific surface receptors and interleukins, and begin to proliferate with many rounds of divisions. In the presence of the repertoire of specific cytokines, activated T cells differentiate into effector T cells that participate in normal immune responses, such as responses directed against foreign pathogens (Swain, S. L. (1999) *Curr. Opin. Immunol.* 11(2): 180-5). When immune system function is impaired, activated T cells may direct immune responses against normal tissues, which causes AD, or against organ transplant, which causes GVHD. Auto-reactive activated T cells infiltrate sites of inflammation in patients with AD and are thought to drive the processes of tissue damage via secretion of pro-inflammatory cytokines, such as INF-$\gamma$, IL-17, IL-23, and TNF-$\alpha$.

The process of T cell activation is tightly regulated. Calcium ions ($Ca^{2+}$) play a critical role in T cell activation. In T lymphocytes, sustained elevation in intracellular calcium concentration ($[Ca^{2+}]_i$) induces a transcriptional program responsible for T cell clonal expansion and secretion of effector cytokines necessary for coordination of the immune response (Negulescu, P. A., Shastri, N., and Cahalan, M. D. (1994) *Proceedings of the National Academy of Sciences of the United States of America* 91(7), 2873-2877; Dolmetsch, R. E., Lewis, R. S., Goodnow, C. C., and Healy, J. I. (1997) Nature 386(6627), 855-858; Dolmetsch, R. E., Xu, K., and Lewis, R. S. (1998) *Nature* 392(6679), 933-936). Conversely, diminished $[Ca^{2+}]_i$ signaling results in impaired T cell activation and, consequently, development of severe immunodeficiency (Gwack, Y., Feske, S., Srikanth, S., Hogan, P. G., and Rao, A. (2007) *Cell Calcium* 42(2):145-56; Feske, S. (2007) *Nat Rev Immunol* 7(9), 690-702).

TCR stimulation, by engagement with foreign antigen, for example, causes a biphasic increase in $[Ca^{2+}]_i$. The first increase results from $Ca^{2+}$ release from intracellular stores. This is a consequence of inositol 1,4,5-trisphosphate ($IP_3$) formation. $IP_3$ binding by the $IP_3$ receptor ($IP_3R$) evokes $Ca^{2+}$ release, predominantly from the endoplasmic recticulum. This first phase is followed by activation of the plasmalemmal store-operated $Ca^{2+}$ (SOC) channels, which allows for the store-operated $Ca^{2+}$ influx (SOCE) across the plasma membrane (Lewis, R. S. (2001) *Annual Review of Immunology* 19, 497-521; Putney, J. W., Jr. (1986) *Cell Calcium* 7(1), 1-12; Putney, J. W., Jr., and McKay, R. R. (1999) *Bioessays* 21(1), 38-46).

Recent studies have identified members of the ryanodine receptor (RyR) family as contributing to the $IP_3$-independent component of $Ca^{2+}$ signaling in some types of immune cells. RyR antagonists ruthenium red and dantrolene inhibit murine T cell proliferation and IL-2 production following TCR stimulation, whereas diminished expression of the type 3 RyR reduces TCR-dependent $[Ca^{2+}]_i$ signaling in Jurkat T cells, a human leukemia cell line derived from a single person (Dupuis, G., and Bastin, B. (1988) *J Leukoc Biol* 43(3), 238-247; Guse, A. H., da Silva, C. P., Berg, I., Skapenko, A. L., Weber, K., Heyer, P., Hohenegger, M., Ashamu, G. A., Schulze-Koops, H., Potter, B. V., and Mayr, G. W. (1999) Nature 398(6722), 70-73; Schwarzmann, N., Kunerth, S., Weber, K., Mayr, G. W., and Guse, A. H. (2002) *J Biol Chem* 277(52), 50636-50642).

In Jurkat T cells TCR activation stimulates production of cyclic adenosine 5'-diphosphate-ribose (cADPR) and/or nicotinic acid adenine dinucleotide phosphate (NAADP), both of which are agonists of the RyR family (Guse, A. H., da Silva, C. P., Berg, I., Skapenko, A. L., Weber, K., Heyer, P., Hohenegger, M., Ashamu, G. A., Schulze-Koops, H., Potter, B. V., and Mayr, G. W. (1999) *Nature* 398(6722), 70-73; Gasser, A., Glassmeier, G., Fliegert, R., Langhorst, M. F., Meinke, S., Hein, D., Kruger, S., Weber, K., Heiner, I., Oppenheimer, N., Schwarz, J. R., and Guse, A. H. (2006) *J. Biol. Chem.* 281(5), 2489-2496). Decreased cADPR levels also reduce the TCR-dependent $[Ca^{2+}]_i$ signaling in Jurkat T cells (Guse, A. H., da Silva, C. P., Berg, I., Skapenko, A. L., Weber, K., Heyer, P., Hohenegger, M., Ashamu, G. A., Schulze-Koops, H., Potter, B. V., and Mayr, G. W. (1999) *Nature* 398(6722), 70-73; Schwarzmann, N., Kunerth, S., Weber, K., Mayr, G. W., and Guse, A. H. (2002) *J. Biol. Chem.* 277(52), 50636-50642). Mechanisms of activation, and the role of RyR in regulation of $[Ca^{2+}]_i$ signaling and $Ca^{2+}$-dependent functions in normal human T cells have not been previously elucidated. Recent studies described in this invention revealed for the first time that RyR are highly expressed in activated human T cells, where they are activated by SOCE and play essential role in controlling $Ca^{2+}$ signaling and $Ca^{2+}$-dependent functions of activated T lymphocytes.

There are three known isoforms of RyR: type 1 (RyR1), type 2 (RyR2), and type 3 (RyR3). The RyR1 and RyR2 were originally found in the sarcoplasmic reticulum of skeletal and cardiac muscles, respectively. $Ca^{2+}$ release from the sarcoplasmic reticulum through these receptors plays a central role in regulating the contraction of skeletal and cardiac muscle fibers. The RyR3 has been detected in specific regions of the brain, nonmuscle tissues, and skeletal muscle as well.

BRIEF SUMMARY OF THE INVENTION

The present invention is based on the surprising finding that RyR are genetically and functionally up-regulated in activated human T cells, and that inhibitors of type 1 and type 3 RyR suppress intracellular $Ca^{2+}$ signaling and $Ca^{2+}$-dependent functions of activated human T lymphocytes. Therefore, inhibitors of RyR1 and/or RyR3 can be used as immunosuppressants and/or for the treatment of T cell-mediated human disorders, such as autoimmune disorders (multiple sclerosis, rheumatoid arthritis), graft versus host diseases (e.g., graft rejection), and inflammation.

The present invention provides methods of treating or preventing a T-cell mediated disorders in humans and animals. The methods comprise administering to the human or animal patient, in the amount and form that is effective to treat or prevent the disease or disorder, a pharmaceutical composition comprising a ryanodine receptor inhibitor and a pharmaceutically acceptable carrier, wherein the patient is not suffering from muscular skeletal dysfunction.

The T-cell mediated disorder can be inflammation, an autoimmune disease, or graft versus host disease. In some embodiments, the autoimmune disease is multiple sclerosis.

In some embodiments, the patient is diagnosed with relapsing-remitting or primary progressive clinically definite multiple sclerosis, or presents a first clinical demyelinating event and multiple sclerosis is highly suspected.

The RyR inhibitor can be any compound or agent that inhibits calcium release from the ryanodine receptor(s). In some embodiments, the RyR inhibitor is specific for type 1 RyR. In some embodiments, the RyR inhibitor is specific for type 3 RyR. In some embodiments, the RyR inhibitor is specific for type 1 and type 3 RyR. In some embodiments, the RyR inhibitor has an affinity for type 1 and/or type 3 RyR at least 10 fold higher than its affinity for type 2 RyR. The RyR inhibitor of the present invention can be administered orally, parenterally, and/or topically.

In some embodiments, the compound is dantrolene, a dantrolene analogue, or a pharmaceutically acceptable salt thereof. An exemplary analogue is azumolene. In some embodiments, the pharmaceutically acceptable salt is a sodium salt. In some embodiments, the pharmaceutically acceptable salt is a quaternary ammonium salt. In some embodiments, the compound is a natural or synthetic ryanoid. In some embodiments, the compound is ryanodine. In other embodiments, an inhibitory nucleic acid molecule, such as an siRNA, can be used to inhibit expression of the ryanodine receptor, e.g., specifically RyR1 and/or RyR3.

The methods are applicable to both human therapy and veterinary applications. In the preferred embodiment the patient is a mammal, preferably a primate, and in the most preferred embodiment the patient is human. In some embodiments, the patient is a non-human.

DEFINITIONS

A ryanodine receptor inhibitor is a compound or agent that inhibits or reduces calcium efflux from the ryanodine receptor. The agent can be a small molecule antagonist such as dantrolene (1-[[[5-(4-nitrophenyl)-2-furanyl]methylene] amino]-2,4-imidaz olidinedione) or a water-soluble analogue thereof, such as azumolene (1-[[[5-(4-bromophenyl)-2-oxazolyl]methylene]amino]-2,4-imida zolidinedione) whose biological activity is conferred to inhibition of RyR1 and/or RyR3, but not RyR2. Other dantrolene analogues useful for the present invention include 1-{[5-(4-Methoxyphenyl)furfurylidene]amino}imidazolidine-2,4-dione, 1-{[5-(3-Methoxyphenyl)furfurylidene]amino}imidazolidine-2,4-dione, 1-{ [5-(2-Methoxyphenyl)furfurylidene]amino}imidazolidine-2,4-dione, 1-[(5-Phenylfurfurylidene)amino]imidazolidine-2,4-dione, 1-{[5-(4-Methylphenyl)furfurylidene] amino}imidazolidine-2,4-dione, 1-{[5-(4-Nitrophenyl) furfurylidene]amino}imidazolidine-2,4-dione, 1-{[5-(3-Nitrophenyl)furfurylidene]amino}imidazolidine-2,4-dione, 1-{[5-(2-Nitrophenyl)furfurylidene]amino}imidazolidine-2,4-dione, 1-{[5-(4-Trifluoromethylphenyl)furfurylidene] amino}imidazolidine-2,4-dione, 1-{[5-(2,3,4,5,6-Pentafluorophenyl)furfurylidene]amino}imidazolidine-2,4-dione, 1-{ [5-(4-Fluorophenyl)furfurylidene]amino}imidazolidine-2, 4-dione, 1-{[5-(4-Phenylphenyl)furfurylidene] amino}imidazolidine-2,4-dione, 1-{[5-(2,6-Dinitrophenyl) furfurylidene]amino}imidazolidine-2,4-dione, 1-{[5-(1-Naphthyl)furfurylidene]amino}imidazolidine-2,4-dione, 1-{ [5-(4-Bromophenyl)furfurylidene]amino}imidazolidine-2, 4-dione, 1-{[5-(4-Hydroxyphenyl)furfurylidene] amino}imidazolidine-2,4-dione, 1-{[5-(4-Trifluoromethanesulfonylphenyl)furfurylidene] amino}imidazolidine-2,4-dione, 1-{[5-(4-Cyanophenyl) furfurylidene]amino}imidazolidine-2,4-dione, 1-{[5-(4-Nitrophenyl)-2-thenylidene]amino}imidazolidine-2,4-dione, 1-{[5-(2-Nitrophenyl)-2-thenylidene] amino}imidazolidine-2,4-dione (Hosoya T, Aoyama H, Ikemoto T, Kihara Y, Hiramatsu T, Endo M, Suzuki M. (2003), Bioorg Med. Chem. 11(5):663-73). Other exemplary small molecule antagonists include 1) ryanoids (e.g. ryanodine (an ester of pyrrole-α-carboxylic acid with ryandolol), 9,21-didehydroryanodine (differs from ryanodine by the absence of two H atoms), or other natural or synthetic biologically active ryanoids; 2) purine derivatives and related compounds (e.g. 4,6-dibromo-3-hydroxycarbazole a carbazole derivative with a carbazole skeleton and bromine at C-6); 3) anthraquinones (e.g. doxorubicin); 4) polyamines: inorganic polyamines (e.g. polycationic dye ruthenium red; tetramine palladium and tetramine platinum), aminoglycoside antibiotics (e.g. neomycin, gentamicin, streptomycin); organic polyamines (e.g. polylysine and polyarginine); 5) FLA365. [2,6-dichloro-4-(dimethylamino)phenyl]-isopropylamine; 6) local anesthetics (e.g. procaine and tetracaine, lidocaine, QX 314); 7) peptides (e.g. imperatoxin-I, helothermine).

Alternatively, the inhibitor can be biological molecule such as an inhibitory nucleic acid, such as antisense nucleic acids, short interfering RNA (siRNA), small hairpin RNA (shRNA), microRNA, ribozymes or similar molecules which downregulate a specific type of RyR (e.g., RyR1 and/or RyR3) gene or protein expression. In some embodiments, the inhibitory nucleic acid is a small interfering RNA that prevents translation of RyR1 and/or RyR3 mRNAs. In some embodiments, the inhibitory nucleic acid is a small hairpin RNA that prevents translation of RyR1 and/or RyR3 mRNAs.

The term "siRNA" refers to a double stranded RNA molecule which prevents translation of a target mRNA. Standard techniques are used for introducing siRNA into cells, including those wherein DNA is used as the template to transcribe RNA. The siRNA comprises a sense nucleic acid sequence and an anti-sense nucleic acid sequence of the polynucleotide of interest. The siRNA is constructed such that a single transcript (double stranded RNA) has both the sense and complementary antisense sequences from the target gene, e.g., a hairpin.

The nucleotide sequence of siRNAs may be designed using an siRNA design computer program available from, for example, the Ambion website on the world wide web. Nucleotide sequences for the siRNA are selected by the computer program based on the following protocol:

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server on the world wide web.
3. Select qualifying target sequences for synthesis. At Ambion, preferably several target sequences can be selected along the length of the gene for evaluation.

The inhibitory nucleic acids of the invention will inhibit the expression of a specific type of RyR and is thereby useful in suppressing its biological activity. In some embodiments, the length of the antisense oligonucleotides and siRNAs is less than or equals to 10 nucleotides. In some embodiments, the length of the antisense oligonucleotides and siRNAs is as long as the naturally occurring the transcript. In some embodiments, the antisense oligonucleotides and siRNAs have 19-25 nucleotides. In some embodiments, the antisense oligonucleotides and siRNAs are less than 75, 50, 25 nucleotides in length.

A "patient" for the purposes of the present invention includes both humans and other animals, particularly mammals.

Muscular skeletal dysfunction, as used herein, refers to conditions associated with weakness and/or wasting of skeletal muscles, which includes symptoms such as lower back pain, joint injuries and various repetitive strain injuries, including upper limb disorder(s) affecting the arms, neck and shoulders.

BRIEF DESCRIPTION OF THE DRAWINGS

FIG. 1. Genetic and functional expression of human RyR1, RyR2, and RyR3 in human peripheral blood mononuclear cell-derived resting and activated T cells. (A), Representative quantitative TaqMan PCR amplification plots for hRyR1 amplification; the fluorescence intensities are plotted as functions of a cycle number. Each TaqMan PCR analysis was performed in duplicates. $C_t$ value, a cycle number in which fluorescence reaches a threshold level (red line), was used for quantification. (B), Quantification of data presented in (A) showing relative expression of hRyR1, hRyR2, and hRyR3 in resting (R, open bars) and activated (A, grey bars) T lymphocytes from nine healthy human donors determined using Real Time TaqMan PCR. B2M housekeeping gene expression was used for normalization. Final quantization was done using the comparative $C_t$ method (User Bulletin #2, Applied Biosys.) and is reported as transcription relative to hRyR1, hRyR2, and hRyR3 cDNA levels in resting T cells from a randomly selected donor. In brief, the housekeeping gene, B2M, was used to normalize the $C_t$ values of the target genes ($\Delta C_t = C_t$(hRyR)−$C_t$(B2M)). The $\Delta C_t$ was calibrated against the $\Delta C_t$ of the target gene (hRyR1, hRyR2, or hRyR3) in resting T cells from a randomly selected donor. The relative linear amount of target molecules relative to the calibrator, was calculated by $2^{-\Delta\Delta Ct}$. (*) indicates that differences between means are significant (p<0.05; independent Student's t test; n=9). n–number of experiments; error bars=S.E. of the means. (C), Time courses of changes in cytosolic $Ca^{2+}$ concentration ($[Ca^{2+}]_i$) in response to RyR agonist caffeine (20 mM) recorded from resting (top panel), or activated human T cells (lower panel), in normal Tyrode extracellular solution. To confirm that caffeine evokes $Ca^{2+}$ release from the RyR, activated T cells were pre-incubated with 400 µM ryanodine (Ry, blue trace), which at this concentration blocks all types of RyR, or vehicle alone (Control, black trace) for 30 min prior to the application of caffeine. Each trace represents an average of 20 traces recorded from the individual cells.

FIG. 2. RyR inhibitor ryanodine (Ry) reduces global $[Ca^{2+}]_i$ elevation during $Ca^{2+}$ readdition and facilitates store refilling in Jurkat T lymphocytes. (A), Average $[Ca^{2+}]_i$ time courses recorded from untreated cells (black traces, control) or cells pre-incubated with Ry (green trace). Extracellular $Ca^{2+}$ was omitted prior to the recordings. Cyclopiazonic acid (CPA, 30 µM) and 2 mM $Ca^{2+}$-containing extracellular solution were applied as indicated. Note that, on average, cells pre-incubated with Ry display reduced $[Ca^{2+}]_i$ transient following $Ca^{2+}$ readdition but enhanced $[Ca^{2+}]_i$ transients induced by the second CPA application. Each trace is an average of 20 traces recorded from the individual cells in a typical experiment. Areas under the $[Ca^{2+}]_i$ traces were integrated to determine amount of global $[Ca^{2+}]_i$ elevation during $Ca^{2+}$ readdition ($[Ca^{2+}]_{SOCE}$) and amount of $Ca^{2+}$ released from the store by application of CPA prior ($CPA_1$) and after ($CPA_2$) $Ca^{2+}$ readdition. Values of $[Ca^{2+}]_i$ prior to the CPA or extracellular $Ca^{2+}$ readdition were subtracted before integration. Ratio of integrated responses to CPA ($CPA_2/CPA_1$) was taken as a measure of store refilling following $Ca^{2+}$ readdition. (B, C), Summarized data from experiments performed as shown in (A). (B), Average $[Ca^{2+}]_{SOCE}$ in untreated cells (open bars; control) and in cells preincubated with Ry (grey bars). (C) Average $CPA_2/CPA_1$ ratio in untreated cells (open bars; control) and in cells pre-incubated with Ry (grey bars). Stars indicate that differences between means are statistically significant (p<0.01, independent Student's t test, n=6; n–number of experiments). (D), Time courses of changes in cytosolic free $Ca^{2+}$ concentration ($[Ca^{2+}]_i$) showing the absence of acute effects of Ry (400 green trace) applied in nominally $Ca^{2+}$-free extracellular solution on. Vehicle (DMSO) alone was applied instead of Ry in control experiments (black trace). Extracellular $Ca^{2+}$ was omitted and ryanodine (Ry, RyR blocker) or cyclopiazonic acid (CPA), a blocker of sarco-endoplasmic reticulum $Ca^{2+}$ ATPase, were applied as indicated. Each trace is an average of 20 traces recorded from individual cells in a typical experiment (n=5, n–number of experiments). (E), Time courses of $Mn^{2+}$ quench of fura-2 fluorescence ($F_i$) in untreated cells (black traces, control) and cells preincubated for 30 min with 400 µM Ry (green traces). Baseline time courses of $Mn^{2+}$ quench of fura-2 fluorescence were recorded in the absence of CPA (upper traces). To record $Mn^{2+}$ influx via SOC channels, 30 µM CPA was applied 10 min prior to $Mn^{2+}$ to deplete the store (lower traces). Each trace is an average of 20 traces recorded from individual cells in a typical experiment (n=5).

FIG. 3. Ryanodine (Ry) downregulates $Ca^{2+}$ responses to T cell receptor (TCR) agonist phytohaemagglutinin P (PHA). (A, B), Average $[Ca^{2+}]_i$ responses to 20 PHA applied as indicated in $Ca^{2+}$-free external solution in cells preincubated with 400 μM Ry (B, blue trace) or vehicles alone (black traces, control). 30 μM CPA or 0.5 mM $Ca^{2+}$-containing solution were applied following PHA as indicated. Each trace represents an average of 20 traces recorded from individual cells. (C–E), Summarized data from experiments performed as shown in (A and B). (C), Average integrated $[Ca^{2+}]_i$ transients evoked by PHA ($[Ca^{2+}]_{PHA}$) in cells preincubated with Ry (grey bars), or vehicles alone (open bars; control). (D), Average integrated $[Ca^{2+}]_i$ transients evoked by CPA ($[Ca^{2+}]_{CPA}$) applied following PHA in cells pre-incubated with Ry (grey bars), or vehicles alone (open bars; control). Brackets in (A and B) indicate the areas that were background-subtracted and integrated to obtain $[Ca^{2+}]_{PHA}$ and $[Ca^{2+}]_{CPA}$ values. (E), Average baseline-subtracted peak values of $[Ca^{2+}]$; transients, shown in (B), evoked by 0.5 mM $Ca^{2+}$ readdition in cells preincubated with Ry (grey bars), or vehicles alone (open bars; control). (*) indicates that differences between means are statistically significant at p<0.01 (independent t test). n–number of experiments.

FIG. 4. RyR inhibitors ryanodine (Ry) and dantrolene (Da) suppress global $[Ca^{2+}]_i$ elevation in activated but not resting human T lymphocytes. (A), Average $[Ca^{2+}]_i$ time courses recorded from resting T cells pre-incubated for 30 minutes prior to the experiment with Ry (500 μM, blue trace), or Da (30 μM, red trace) or vehicles alone (MetOH or EtOH; control, black trace). Each trace is an average of 18-20 traces recorded from individual cells in a typical experiment. Representative traces from one of seven experiments performed on resting T cells from five different donors. (B), Average $[Ca^{2+}]_i$ time courses recorded from activated T cells preincubated for 30 minutes prior to the experiment with vehicles alone (MetOH or EtOH; control, black trace). or Ry (500 μM, blue trace) or Da (30 μM, red trace). CPA (30 μM), and 2 mM $Ca^{2+}$ were applied as indicated. To obtain activated T cell population, resting T cells where stimulated in vitro with immobilized anti-CD3 antibodies (Ab) and soluble anti-CD28 Ab (anti-CD3/CD28 Ab) for 72-96 h. Each trace is an average of 18-20 traces recorded from the individual cells in a typical experiment. Representative traces from one of seven experiments performed on activated T cells from five different donors. (C), Summarized effects of RyR blockers Ry (500 μM) and Da (30 μM) on global $[Ca^{2+}]_i$ elevation following activation of SOCE ($[Ca^{2+}]_{SOCE}$) in activated human T cells. $[Ca^{2+}]_{SOCE}$ was determined by integration of the area under the $[Ca^{2+}]_i$ trace during readdition of extra cellular $Ca^{2+}$ following CPA wash out as shown in (A and B). Values of $[Ca^{2+}]_i$ prior to the extracellular $Ca^{2+}$ readdition were subtracted before integration. (*) indicate that differences between means are statistically significant (p<0.01, independent Student's t test; n=7). n=number of experiments; error bars=S.E. of the means.

FIG. 5. RyR inhibitors ryanodine (Ry) or dantrolene (Da) inhibit Jurkat and normal human activated T cell proliferation and IL-2 production. (A), The fluorescence profile of CFSE-loaded Jurkat T cells (top panels) and human T cells (lower panels) incubated for 72 hours in the presence of 400 μM Ry (left panels; shaded histograms) or 30 μM Da (right panels; shaded histograms), or vehicles alone (control, open histograms in all panels). The dashed lines show the fluorescence profiles of CFSE-loaded cells incubated for 12 hours in FBS-deprived media (undivided cell population at time 0). The brackets and numbers above the brackets indicate an estimated fraction of undivided cells in control cell populations and cell populations incubated with Ry or Da. Representative data from five experiments performed with each blocker. (B), IL-2 content in Jurkat T cell culture supernatants. Cells were incubated for 24 hours in cell culture media supplemented with 20 μM PHA alone or in combination with Ry (400 μM) or Da (30 μM), as indicated with (+); or vehicles alone, as indicated with (−). The Ry or Da were applied 30 min prior to the PHA. (*) indicates that differences between means are statistically significant at p<0.01 (independent Student's t test, n=6 for each type of experiments).

FIG. 6. Simplified hypothetical scheme of $Ca^{2+}$ dynamics in T cells upon TCR activation. (A), Diagram of intracellular $Ca^{2+}$ dynamics in T cells following TCR activation. (B), proposed mechanism of immunosuppressive action of RyR inhibitors (e.g. ryanodine, dantrolene, azumolene, RyR siRNA, etc): inhibition of RyR reduces intracellular $Ca^{2+}$ elevation following TCR engagement, which in turn leads to incomplete gene transcription program and inhibition or modification of T cell activation or differentiation. Abbreviations: TCR—T cell receptor, A—antigen, $IP_3R$—inositol 1,4, 5-trisphosphate receptor, RyR—ryanodine receptor; SOC—store-operated $Ca^{2+}$ channel, ER—endoplasmic reticulum. SERCA and PMCA are omitted for simplicity.

DETAILED DESCRIPTION

The immune system is a collection of biological processes within an organism that protects against disease by identifying and killing pathogens and tumor cells. It detects a wide variety of agents, from viruses to parasitic worms, and needs to distinguish these from the organism's own healthy cells and tissues in order to function properly.

The immune system can cause disease and harm to the organism. Autoimmunity results from a hyperactive immune system attacking normal tissues as if they were foreign organisms. Even when the immune system is functioning normally, it can have detrimental effects on the organism. The immune system is responsible for the destruction of organ transplants, the so called graft versus host disease (GVHD).

Autoimmune diseases are characterized by T and B lymphocytes that aberrantly target self-proteins and/or other self-molecules causing injury and or malfunction of an organ, tissue, or cell-type within the body (for example, pancreas, brain, thyroid or gastrointestinal tract). Autoimmune diseases include diseases that affect specific tissues as well as diseases that can affect multiple tissues. The characteristic feature of tissue-specific autoimmunity is the selective targeting of a single tissue or individual cell type. Nevertheless, certain autoimmune diseases that target ubiquitous self-proteins can also effect specific tissues.

T-lymphocytes are believed to contribute to the development of a number of autoimmune disease. Table 1 provides a non-exhaustive list of autoimmune diseases or disorders caused by T cells.

TABLE 1

| Nervous System |
| --- |
| Multiple sclerosis |
| Myasthenia gravis |
| Autoimmune neuropathies such as Guillain-Barré |
| Autoimmune uveitis |
| Ophthalmologic: |
| Uveitis |

TABLE 1-continued

Blood:

Autoimmune hemolytic anemia
Pernicious anemia
Autoimmune thrombocytopenia
Vascular:

Temporal arteritis
Anti-phospholipid syndrome
Vasculitides such as Wegener's granulomatosis
Behcet's disease
Atherosclerosis
Skin:

Psoriasis
Dermatitis herpetiformis
Pemphigus vulgaris
Vitiligo
Pemphigus Vulgaris
Mycosis Fungoides
Allergic Contact Dermatitis,
Atopic Dermatitis
Lichen Planus
PLEVA (Pityriasis lichenoides et
varioliforms acuta),
Gastrointestinal Tract Crohn's Disease
Ulcerative colitis
Primary biliary cirrhosis
Autoimmune hepatitis
Endocrine:

Type 1 diabetes mellitus
Addison's Disease
Grave's Disease
Hashimoto's thyroiditis
Autoimmune oophoritis and orchitis
Autoimmune Thyroiditis
Multiple Organs and/or Musculoskeletal System:

Rheumatoid arthritis
Systemic lupus erythematosus
Scleroderma
Polymyositis
Dermatomyositis
Spondyloarthropathies such as ankylosing spondylitis
Sjogren's Syndrome A Prototypic Autoimmune Disorder: Multiple Sclerosis Multiple sclerosis (MS; also known as disseminated sclerosis or encephalomyelitis disseminata) is an autoimmune disease affecting the nervous system. In MS the immune system attacks and damages myelin, a protein which surrounds nerve cells. This damage disrupts the ability of nerve cells in the brain and spinal cord to communicate with each other.

MS is the most common disabling neurologic disease in people ages 18 to 60. Disease onset usually occurs in young adults, and it is more common in females. What triggers MS remains unknown.

A. MS Symptomology

Initial MS symptoms usually present themselves as episodic acute periods of worsening (relapsing-remitting from the disease) and can vary depending on which part of the nervous system has been affected, and degree of neuron distraction (Compston, A, et al. McAlpine's Multiple Sclerosis. 3d ed. London: Churchill Livingston; 1998; Clanet, Michel G.; Brassat, David *Curr Opin Neurol* 2000 June; 13(3):263-70; MS Society Symptom Management Survey. London: MS Society; 1997; Noseworthy J. H., Lucchinetti C., Rodriguez M., et al. 2000. Multiple sclerosis. *N Engl J Med,* 343: pp 938-952; Simon, J H, 2006, Update on Multiple Sclerosis, *Radiol Clin N Am,* 44: 79-100). At the onset of disease or, at the initial stage of relapsing remitting period, symptoms can include optic neuritis, nystagmus resulting from internuclear ophthalmoplegia, and an electrical sensation extending down the back and legs with flexion of the neck. Patients may also present with different neurologic symptoms, including diplopia, bladder dysfunction, vertigo, weakness, paresthesias, and sensory loss. As the disease progresses, the symptoms tend to worsen and other symptoms such as weakness, stiffness, proprioceptive loss of the lower limbs and locomotor ataxia become more significant. The last and most debilitating stages of disease include symptoms secondary to the loss of major neurological functions: spasticity and spasms, urinary incontinence and tract infections, action or truncal tremor, paralysis and pressure sores, nystagmus and abnormal eye movements, neurological chronic pain and cognitive impairment.

B. Guidelines for Diagnosis

The most current guidelines for diagnosing clinically definite multiple sclerosis (CDMS) came from the deliberations of the International Panel on the Diagnosis of Multiple Sclerosis and are known as the McDonald criteria (McDonald W. I., Compston A., Edan G., et al. 2001. Recommended diagnostic criteria for multiple sclerosis: guidelines from the International Panel on the Diagnosis of Multiple Sclerosis. *Ann Neurol* 50: pp 121-127; Polman C H, Reingold S C, Edan G, et al., 2005. Diagnostic criteria for multiple sclerosis: 2005 revisions to the "McDonald Criteria." *Ann Neurol;* 58:840-846). They use a combination of clinical symptoms, MRI observations and other objective laboratory findings to establish dissemination of disease in time and space typical for MS.

The McDonald criteria allow for an earlier diagnosis of CDMS but are criticized for being too rigorous, leading to the case in which CDMS remains undiagnosed despite growing clinical symptoms (Woo D A et al. (2006) Diagnosis and Management of Multiple Sclerosis: Case Studies. *Neurologic Clinics* 24(2):199-214). Therefore, other criteria and predictors for CDMS continue to emerge. The MRI findings at symptom onset were found to be the most important predictor of conversion to CDMS. The late multiphasic disease was found to be associated with disseminated lesions in combination with the optic nerve at the onset of disease, whereas a normal MRI is associated with a lower risk of conversion to CDMS (Frohman E M, Goodin D S, Calabresi P A, et al., the utility of MRI in Suspected MS: report of the Therapeutics and Technology Assessment Subcommittee for the American Academy of Neurology. *Neurology.* 61:602-611).

The earliest clinical presentation of relapsing-remitting MS is a single attack of a single symptom, which is termed a clinically isolated syndrome (CIS). The CIS is suggestive of demyelination but two or more attacks disseminated in time are necessary to fulfill the McDonald criteria for MS diagnosis.

Although exact conversion rates of all CIS to CDMS are not known, it was shown that the risk of conversion from optic neuritis to CDMS during 10 years following initial episode ranged from 22% to 56% (Beck R. W., Trobe J. D., Moke P. S., et al. 2003. High- and low-risk profiles for the development of multiple sclerosis within 10 years after optic neuritis. *Arch Ophthalmol.,* 121: pp 944-949). Furthermore, a review by the Therapeutics and Technology Assessment Subcommittee of the American Academy of Neurology, demonstrated hidden disease activity in 50 to 80% of patients at the time of the first clinical presentation.

C. Protocols for Treating Multiple Sclerosis

Patients with MS are usually categorized into the following four groups:
1. Relapsing-remitting (RR) disease is the most common initial course of the disease which occurs at onset in 80% of cases and is characterized by acute attacks followed by remissions between attacks.
2. In 50% to 80% of patients with RR disease, progressive deterioration with less marked attacks occurs within 10 years of onset; the disease in these patients is called secondary progressive phase MS (SP-MS).
3. Primary progressive MS (PP-MS) occurs in 10% to 15% of patients and is characterized by progressive deterioration from the outset without relapses.
4. Approximately 6% of patients have progressive-relapsing MS (PP-MS) wherein patients experience relapses in parallel with the steady disease progression.

The treatment of MS has three main components: disease modifying treatments, relapse treatments, and symptoms management. The disease modifying treatments aim to reduce the risk of relapse number and severity, the development of new brain or spinal cord lesions, and the progression of neurologic disability. The disease modifying treatments exert their effects through an anti-inflammatory, immunomodulatory, or immunosuppressive mechanisms. Because of the progressive nature of the MS, the disease modifying treatments are most effective when started at the onset of the disease.

The patient may benefit from the disease modifying treatments even if they do not completely fulfill the McDonald criteria for CDMS. Therapy can be started if MS is highly suspected and other diseases have been reasonably excluded. For example, two randomized, controlled trials demonstrated a treatment benefit in patients with a CIS and MRI abnormalities suggestive that MS patients benefited from treatment with interferon β (IFNβ) (Jacobs L D, Beck R W, Simon J H, et al. 2000. Intramuscular interferon beta-1a therapy initiated during a first demyelinating event in multiple sclerosis. *N Engl J Med;* 343: 898-904; Comi G, Filippi M, Barkhof F, et al. 2001. Effect of early interferon treatment on conversion to definite multiple sclerosis: a randomized study. *Lancet;* 357: 1576-1582. These results support the use of the disease modifying treatments after a first clinical demyelinating event and indicate that there may be modest beneficial effects of immediate treatment compared with delayed initiation of treatment.

Organ Transplantation

A common complication in tissue and organ transplantation in humans is immunological incompatibility between the tissue transplant and the host. Graft versus host disease (GVHD) causes significant morbidity and mortality in patients receiving transplants containing allogeneic hematopoietic cells. It is well established that the greater the matching of the MHC class I and II (HLA-A, HLA-B, and HLA-DR) alleles between donor and recipient the better the graft survival and fewer complications with GVHD. Approximately 50% of patients receiving a transplant from a HLA-matched sibling will develop moderate to severe GVHD, and the incidence is much higher in non-HLA-matched grafts. One-third of patients that develop moderate to severe GVHD will die as a result. T lymphocytes and other immune cell in the donor graft attack the recipients' cells that express polypeptides variations in their amino acid sequences, particularly variations in proteins encoded in the major histocompatibility complex (MHC) gene complex on chromosome 6 in humans. GVHD is treated with glucocorticoids, cyclosporine, methotrexate, fludarabine, and OKT3.

Modalities for Treating Immune Cell Mediated Disease

Currently available therapies for these immune cell mediated diseases (e.g., autoimmunity, GVHD) are largely unsatisfactory and typically involve the use of glucocorticoids (e.g. methylprednisolone, prednisone), non-steroidal anti-inflammatory agents, gold salts, methotrexate, antimalarials, and other immunosuppressants such as cyclosporin and FK-506. The usefulness of these agents is limited often by severe side effects such as liver and renal damage. Furthermore, not all patients are responsive to all therapies. For example, it is known that 30% of multiple sclerosis patients are non-responsive to β-interferon (Bertolotto, A. and Gilli, F. (2008). Interferon-beta responders and non-responders. A biological approach. *Neurological Sciences Official Journal of the Italian Neurological Society and of the Italian Society of Clinical Neurophysiology.* 29 Suppl. 2: S216). Additionally, for Multiple Sclerosis in particular, the current therapy with interferon-beta and copaxone only benefits about 60% of patients. The appearance of neutralizing antibodies in around 40% of patients treated with interferon-beta makes interferon-beta treatment less effective over time in the responsive patients. As a result, the vast majority of AD patients continue to accrue progressive disability despite immunomodulatory therapies. Moreover, approximately 50% of patients receiving a transplant from a HLA-matched sibling develop moderate to severe GVHD, and the incidence is much higher in non-HLA-matched grafts. One-third of patients that develop moderate to severe GVHD will die as a result. Finally, the pathogenesis of AD and GVHD is complex and may be heterogeneous across patients or in individual patients over time. A combination regimen could potentially treat multiple distinct pathogenic mechanisms better than any single agent. Therapies with partial efficacy alone could have additive or synergistic efficacy in combination and allow for lower doses with decreased adverse effects.

A ryanodine receptor inhibitor, e.g., a compound or agent that inhibits or reduces calcium efflux from the ryanodine receptor, can be used in the methods of the present invention for treating or preventing a T-cell mediated disorder. In some embodiments, the inhibitor inhibits all isotypes of RyR. In some embodiments, the inhibitor is an inhibitor specific for a subset of RyR5. For example, inhibitors useful for the present invention include RyR inhibitors specific for RyR1, RyR3, or both. In some embodiments, the inhibitor does not inhibit RyR2.

In some embodiments, selective inhibitors of the RyR1 and RyR3, such as dantrolene or azumolene, are less likely to cause such side effects and, thus, may be used alone or in combination with other agents (e.g., cyclosporin and/or FK506) to treat autoimmune diseases and/or GVHD. Thus, the RyR1 and RyR3 inhibitors disclosed herein may provide substantial improvements in the treatment of autoimmune diseases and/or GVHD.

Still further in accordance with the present invention, there are provided methods for causing a desired inhibition of RyR1 and/or RyR3 while not causing undesired inhibition of RyR2 (cardiac type) in a human or animal subject. Such methods generally comprise the RyR blockers that a) selectively inhibit RyR1 and/or RyR3 while b) not causing inhibition of RyR2.

The "desired inhibition of RyR1 and/or RyR3" can be, for example, any inhibition of RyR1 and/or RyR3 that causes an intended therapeutic or preventative effect, such as suppression of function of RyR1 and/or RyR3 in T lymphocytes to treat or prevent a T cell-mediated disorder in the human or animal patient. The "undesired inhibition of RyR2" can be, for example, any inhibition of a RyR2 that causes cardiac side effects, untoward effect or any effect other than the desired therapeutic or preventative effect, such as the inhibition of RyR2 in a way that causes a proarrhythmic effect or increases the potential for cardiac arrhythmia in the human or animal patient.

The agents that inhibit ryanodine receptors can be administered by a variety of methods including, but not limited to parenteral (e.g., intravenous, intramuscular, intradermal, intraperitoneal, and subcutaneous routes), topical, oral, local, or transdermal administration. These methods can be used for prophylactic and/or therapeutic treatment.

As noted above, inhibitors of the invention can be used to treat T-cell mediated disorders. The compositions for administration will commonly comprise a inhibitor dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate water solubility and/or physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that the inhibitors of the invention (e.g. azumolene) when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Further in accordance with the present invention, there are provided pharmaceutical preparations for administering to human or veterinary patients, said preparations comprising RyR blockers such as above or a pharmaceutically acceptable carriers, excipients and other ingredients commonly used in pharmaceutical preparations for oral, rectal, intravenous, intraarterial, intradermal, subcutaneous, intramuscular, intrathecal, sublinginual, bucal, intranasal, trans-mucosal, trans-dermal, topical, other enteral, other parenteral and/or other possible route(s) of administration.

The compositions containing inhibitors of the invention can be administered for therapeutic or prophylactic treatments. In therapeutic applications, compositions are administered to a patient suffering from a disease (e.g., an autoimmune disease) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of an inhibitor that is capable of preventing or slowing the development of a disease in a patient is referred to as a "prophylactically effective dose." The particular dose required for a prophylactic treatment will depend upon the medical condition and history of the patient, the particular disease being prevented, as well as other factors such as age, weight, gender, administration route, efficiency, etc. Such prophylactic treatments may be used, e.g., in a patient who has previously had a disease to prevent a recurrence, or in a patient who is suspected of having a significant likelihood of developing the disease.

EXAMPLES

The following examples are offered to illustrate, but not to limit the claimed invention.

Example 1

Overexpression of RyR1 Gene Expression in Activated Human T Cells Compared with Resting Human T Cells Experimental Procedures Cell Cultures and Chemicals—

All studies involving human subjects were performed after approval by UC Davis Institutional Review Board and after all subjects gave written informed consent. Resting $CD3^+$ human lymphocytes were isolated from the peripheral blood of healthy consented adults using RosetteSep™ human lymphocyte enrichment kit (Stem Cell Tech.) following the manufacturer's instructions. Resting T cells were resuspended at $0.5-1\times10^6$ cells/ml in RPMI 164 medium supplemented with 10 mM HEPES, 10% fetal bovine serum, 2% L-glutamine, 2% vitamins solution, 1% RPMI amino acids solution, and 0.01% β-mercaptoethanol and maintained in suspension in 5% $CO_2$ at 37° C. Resting T cells were activated on the day of isolation by incubation with either PHA (5-20 μM) or anti-CD3 antibody coated onto the tissue culture plates and soluble anti-CD28 antibody (5 m/ml; BD Biosciences). Resting T cells were taken for analysis on the day of isolation, whereas activated T cells were tested 4-5 days after activation.

Human acute T cell leukemia line, Jurkat E6-1 (ATCC, Manassas, Va.), was maintained in cell culture media containing RPMI 1640 medium (Lonza/BioWhittaker, Basel, Switzerland), 10% FBS (Omega Scientific, Tarzana, Calif.), 2% L-glutamine, 2% vitamins solution, 1% RPMI amino acids solution, and 0.01% β-mercaptoethanol. Cells were kept in suspension in 5% $CO_2$ at 37° C. and passaged every 2 days.

Real-Time PCR—

Cells were lysed and relative quantifications of the expression levels of human RyR1, RyR2, and RyR3 were performed using Real Time TaqMan PCR assays using AB Primer Express 2 software and commercially available TaqMan human gene expression assay kits. The housekeeping gene B2M was used for normalization. The human Real Time TaqMan® PCR assays used for B2M (Hs99999907m1), hRyR1 (Hs00166991m1), hRyR2 (Hs00892902m1), and hRyR3 (Hs01044126m1) were ordered directly from Applied Biosystems as inventoried gene expression assays. All assays were run in duplicates.

Data Analysis—

Statistical analysis was performed using Origin 7 software (OriginLab, Northampton, Mass.). All data are presented as the mean±standard error of the mean; n=number of experiments. Statistical differences between means were accepted as statistically significant at p<0.05, using Student's independent t test.

Results

Figure 1:
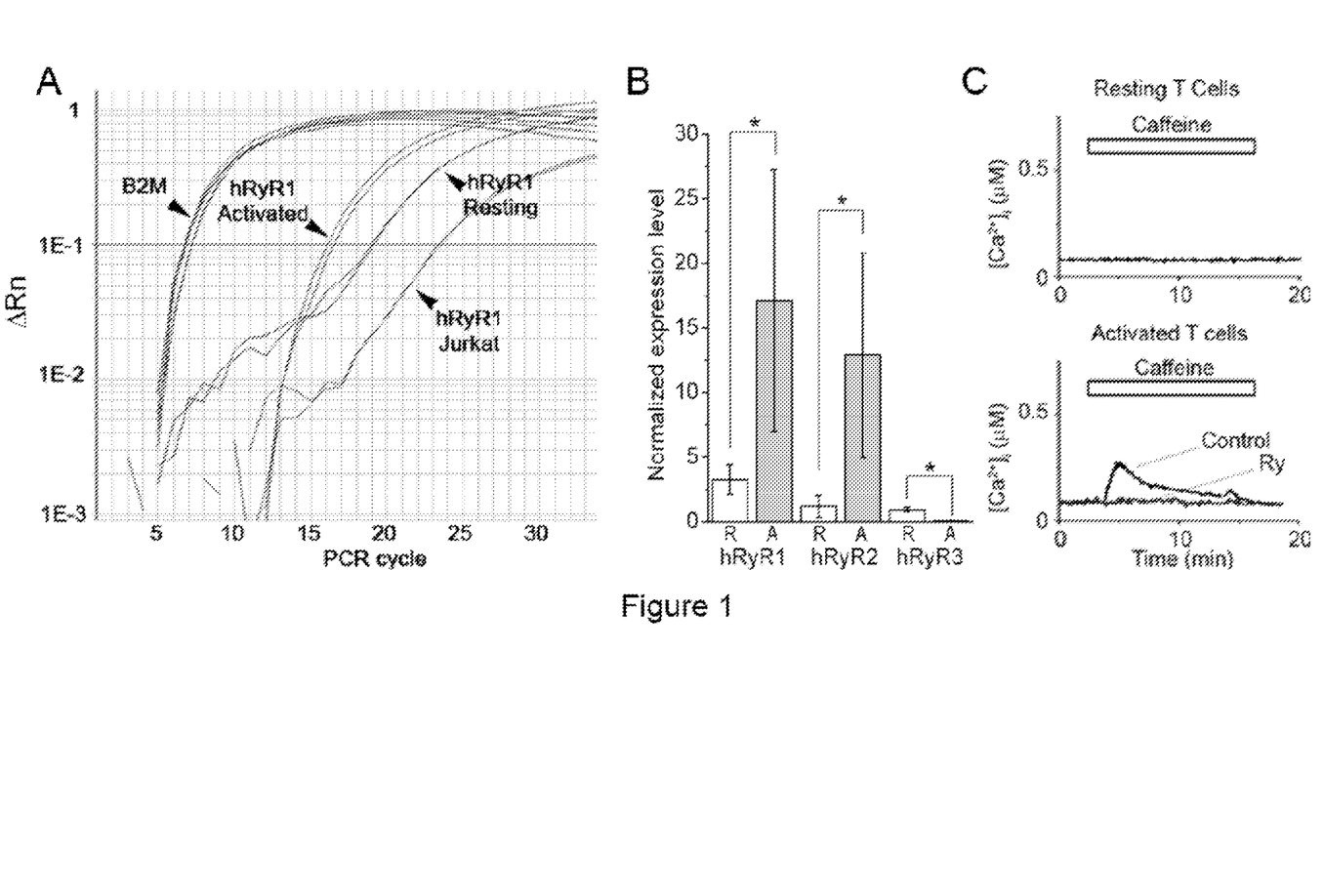

Resting T cells express at low level all three isoforms of RyR (RyR1, RyR2, and RyR3), whereas the expression of RyR1 and RyR2 is significantly upregulated in activated T cells compared with resting (>5 and >10 times, respectively; n=9) (FIG. 1 A, B). Interestingly, RyR3 was expressed at low level in resting T cells, whereas its expression was not detectable in activated T cell from 6 out of 9 donors tested. Jurkat T cells express only RyR3 (not shown), which is consistent with a previous reports (Guse A H, da Silva C P, Berg I, Skapenko A L, Weber K, Heyer P, Hohenegger M, Ashamu G A, Schulze-Koops H, Potter B V, Mayr G W. (1999) Nature (398) 70-73; Hakamata Y, Nishimura S, Nakai J, Nakashima Y, Kita T, Imoto K. (1999) FEBS Lett. (352) 206-210). Thus, these data indicate that activated human T cells overexpress the skeletal muscle-type hRyR1. Therefore, RyR1inhibitors can be used to block RyR1 in activated human T cells to reduce their pathogenic potential in autoimmune diseases and graft vs. host disease. Although RyR3 is expressed at low level in resting and activated T cells, the RyR3 potentially may be overexpressed in specific effector T cell subsets and, therefore, inhibition of RyR3 potentially may have immunosuppressive effect.

Example 2

RyR Blockers Ryanodine and Dantrolene Suppress Cytosolic $Ca^{2+}$ Signaling in T Cells Experimental Procedures Calcium Imaging—

Cell cultures and chemicals were as described in the Example 1. Before experiment, cells were plated on poly-l-lysine-coated glass-bottom clambers and then loaded with 1 μM fura-2/AM and pluronic F-127 for 5 min in modified Tyrode solution containing (in mM): 130 NaCl, 5.6 KCl, 1 $MgCl_2$, 2 $CaCl_2$, 10 HEPES, 10 D-glucose; pH 7.3. After washing, cells were incubated for additional 30 min at 37° C. Some cells were incubated in Modified Tyrode solution containing 400 μM Ry, 30 μM dantrolene, or vehicles (methanol or, ethanol, or DMSO) alone for 30 min at 37° C. In nominally $Ca^{2+}$-free solution, $Ca^{2+}$ was omitted.

Fluorescence images were acquired from adherent cells using a SenSys CCD camera (Roper Scientific, Tucson, Ariz.) and a 40× oil immersion Zeiss objective on a Zeiss Axiovert 200 inverted microscope (Thornwood, N.Y.). Lambda DG-4 filter changer (Sutter Instrument, Novato, Calif.) was used for switching between 340 and 380 nm excitation wavelengths. All experiments were performed at room temperature. Solution exchange was performed via a gravity-driven perfusion system. Solution exchange in the recording chamber was completed within 5 s. The vehicles-containing solutions (methanol or DMSO) were applied in place of the drugs in all control experiments. Data acquisition was performed using MetaFluor v7.0 software (Universal Imaging, Downingtown, Pa.). $[Ca^{2+}]_i$ values were estimated from fura-2 calibration as described previously (Grynkiewicz, G., Poenie, M., and Tsien, R. Y. (1985) J Biol Chem 260(6), 3440-3450). $K_d$ was taken as 248 nM (Fanger, C. M., Neben, A. L., and Cahalan, M. D. (2000) J Immunol 164(3), 1153-1160). Unless otherwise indicated, in each experiment changes in $[Ca^{2+}]_i$ were recorded from 15-20 cells and then averaged.

Manganese Quench of Fura-2 Fluorescence—

Because $Mn^{2+}$ readily passes through SOC channels (Missiaen, L., Declerck, I., Droogmans, G., Plessers, L., De Smedt, H., Raeymaekers, L., and Casteels, R. (1990) J Physiol 427, 171-186) and is unlikely to be transported from the cytosol (Chiesi, M., and Inesi, G. (1980) Biochemistry 19(13), 2912-2918; Chiesi, M., and Inesi, G. (1981) Arch Biochem Biophys 208(2), 586-592), the rate of fura-2 quenching in the presence of $Mn^{2+}$ was used as a measure of divalent cation influx into the bulk cytoplasm in intact cells. The extracellular solution used in all $Mn^{2+}$ quench experiments contained (in mM): 130 NaCl, 5.6 KCl, 1 $MgCl_2$, 0.3 $CaCl_2$, 0.5 $MnCl_2$, 10 HEPES, 10 D-glucose; pH 7.3. Changes in $Ca^{2+}$-independent fluorescence due to $Mn^{2+}$ quench were determined using method described by Zhou & Neher (Zhou, Z., and Neher, E. (1993) J Physiol 469, 245-273). Briefly, background corrected fura-2 fluorescence excited at 340 nm ($F_{340}$) was plotted against background corrected fura-2 fluorescence excited at 380 nm ($F_{380}$) during the initial 10 seconds following application of 30 μM cyclopiazonic acid (CPA). The slope of the $F_{340}$ versus $F_{380}$ relationship equals the 'isocoefficient' α. The fluorescence value, $F_i$, which is unaffected by changes in $[Ca^{2+}]_i$, was determined as: $F_i=F_{340}+\alpha F_{380}$. The rate of $F_i$ decline is proportional to the rate of $Mn^{2+}$ entry into the cytosol and was used as an indicator of plasma membrane $Ca^{2+}$ permeability.

Data Analysis—

Image analysis was performed using MetaFluor v7.0 software (Universal Imaging). Further measurements and statistical analysis were performed using Origin 7 software (OriginLab, Northampton, Mass.). All data are presented as the mean±standard error of the mean; n=number of experiments. Statistical differences between means were accepted as statistically significant at p<0.05, using Student's paired or unpaired t tests.

Results

RyR Inhibitors Reduce Global $[Ca^{2+}]_i$ Elevation in Jurkat T Cells.

Fluorescent $Ca^{2+}$ indicator fura-2, cyclopiazonic acid (CPA), a reversible inhibitor of sarco-endoplasmic reticulum $Ca^{2+}$-ATPase (SERCA), and ryanodine (Ry), an alkaloid which specifically blocks all types of RyR (Gafni, J., Munsch, J. A., Lam, T. H., Catlin, M. C., Costa, L. G., Molinski, T. F., and Pessah, I. N. (1997) Neuron 19(3), 723-733; Zucchi, R., and Ronca-Testoni, S. (1997) Pharmacol Rev 49(1), 1-51) were employed to explore the contribution of $Ca^{2+}$ release from the RyR into the global $[Ca^{2+}]_i$ dynamics in Jurkat T cells.

Figure 2:
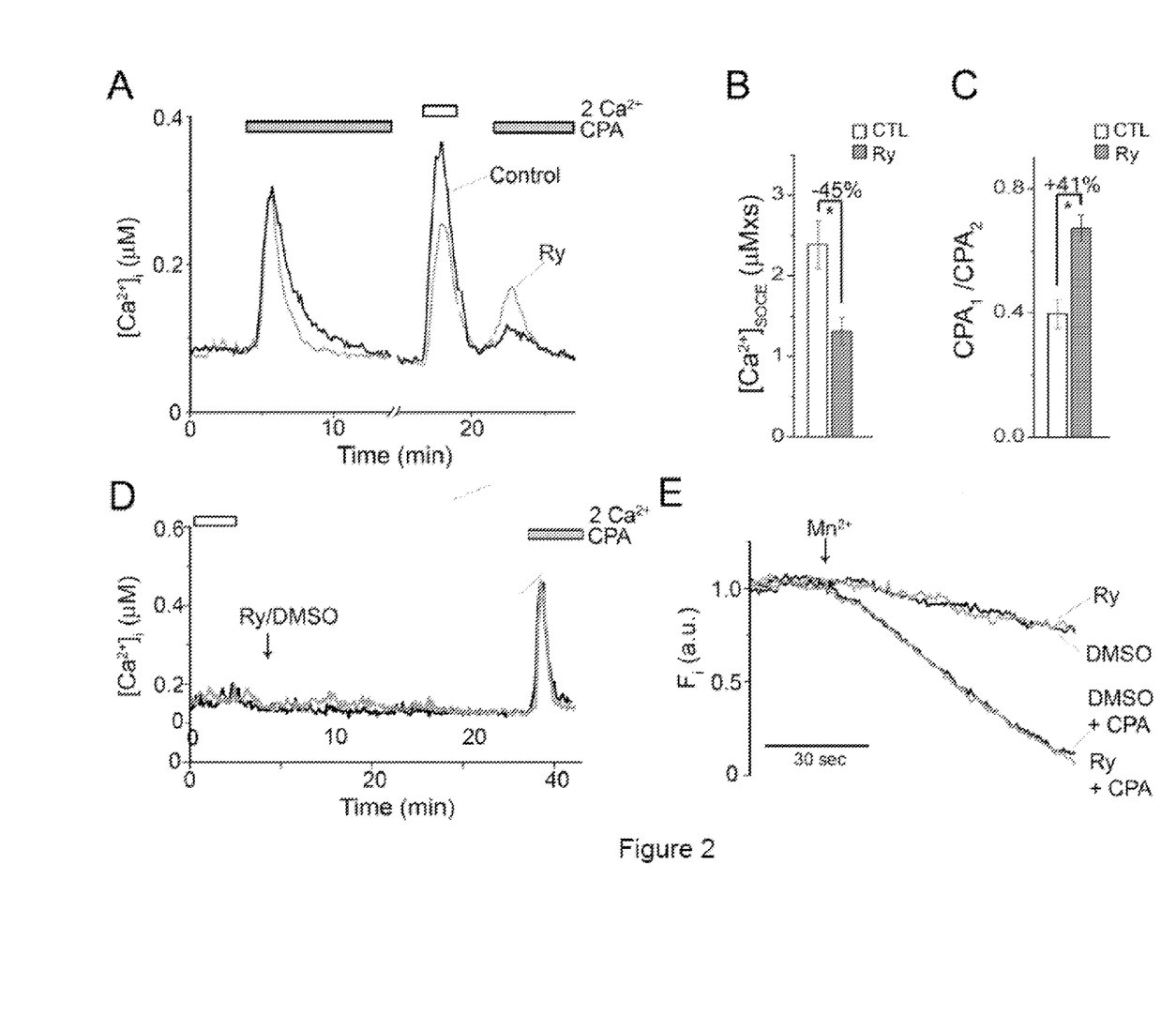

When CPA was applied in $Ca^{2+}$-free solution, a transient elevation in $[Ca^{2+}]_i$ due to $Ca^{2+}$ release via "leak" channels was observed (FIG. 2A). Readdition of extracellular $Ca^{2+}$ following first CPA application produced a global elevation in $[Ca^{2+}]_i$ due to $Ca^{2+}$ entry via SOC channels. After removing of extracellular $Ca^{2+}$, the second application of CPA evoked $[Ca^{2+}]_i$ transients, indicating that the store was refilled during extracellular $Ca^{2+}$ readdition. The $[Ca^{2+}]_i$ transients evoked by the first application of CPA were similar in shape and magnitude in both untreated cells (control) and cells preincubated with Ry (FIG. 2A). However, the $[Ca^{2+}]_i$ transients during $Ca^{2+}$ readdition were significantly smaller in Ry-treated cells compared with control.-Furthermore, CPA application following $Ca^{2+}$ readdition produced larger $[Ca^2]_i$ transients, in Ry-treated cells compared with untreated cells.

Integration of $[Ca^{2+}]_i$ transients evoked by SERCA blockers has been shown to provide an accurate estimate of releasable store content (Bergling, S., Dolmetsch, R., Lewis, R. S., and Keizer, J. (1998) Cell Calcium 23(4), 251-259). The ratio of background-subtracted integrated $[Ca^{2+}]_i$ transients induced by the second CPA application (CPA$_2$) to the first one (CPA$_1$) (FIG. 2A) was taken as measure of the extent of store refilling. The $[Ca^{2+}]_i$ transients recorded during $Ca^{2+}$ readdition induced by SOCE were also integrated and denoted as $[Ca^{2+}]_{SOCE}$. Summarized data presented in FIG. 2 show that application of Ry significantly downregulated $[Ca^{2+}]_i$ transients evoked by $Ca^{2+}$ readdition (FIG. 2 B) but facilitated store refilling (FIG. 2C) in Jurkat T lymphocytes.

When applied extracellularly, Ry does not induce $Ca^{2+}$ release (FIG. 2 D) or affect divalent ction influx (FIG. 2 E), which confirmed that inhibition of $Ca^{2+}$ release from RyR accounts for the reduction in $[Ca^{2+}]_i$ elevation during $Ca^{2+}$ readdition in cells preincubated with Ry. Thus, activation of $Ca^{2+}$ release from RyR contributes significantly into global $[Ca^{2+}]_i$ elevation in Jurkat T cells.

Inhibition of RyR Downregulates $[Ca^{2+}]_i$ Signaling Following TCR Stimulation in Jurkat T Cells.

Figure 3:
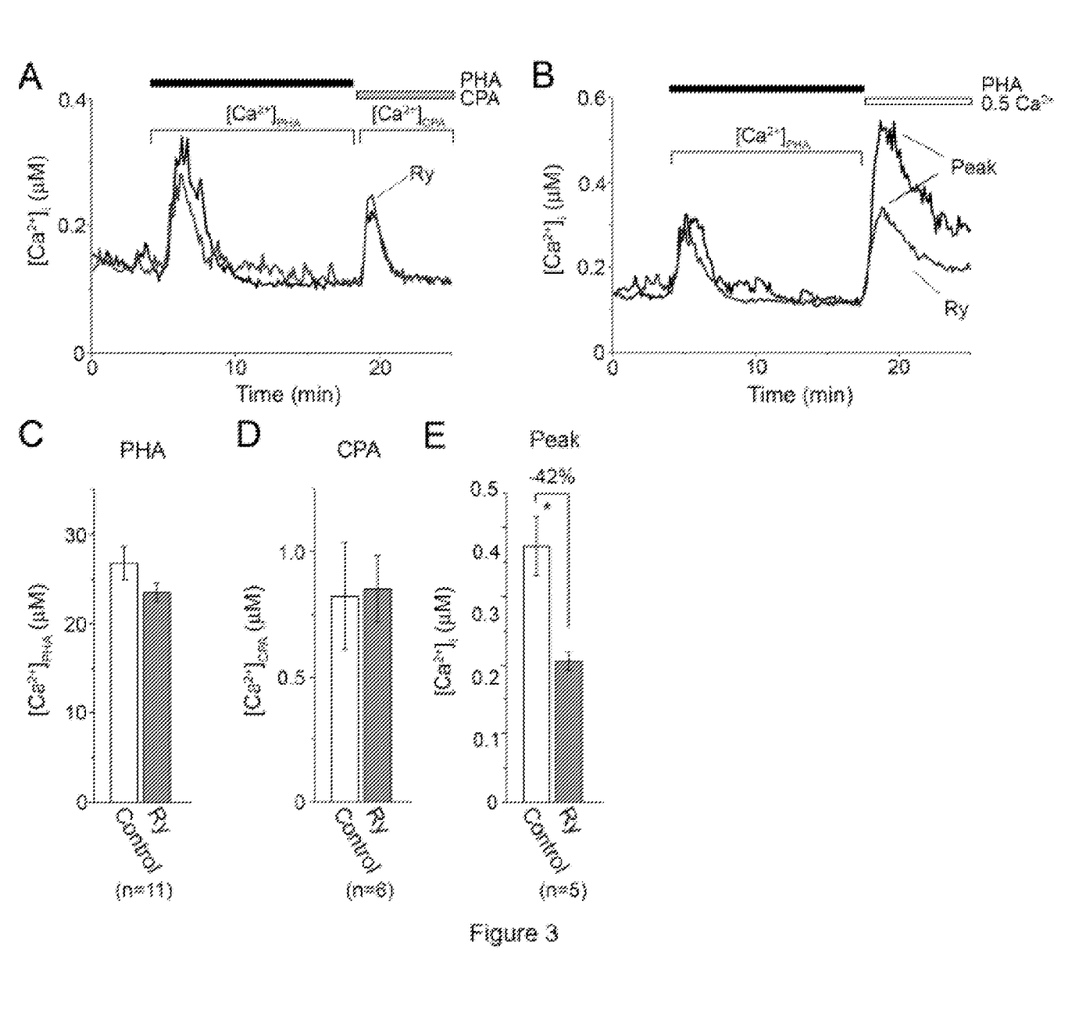

In the absence of extracellular $Ca^{2+}$, a TCR agonist PHA evokes $[Ca^{2+}]_i$ elevation due to the $Ca^{2+}$ release from the intracellular store (FIG. 3 A, B). Pre-incubation with Ry did not significantly affect the PHA- or CPA-induced $[Ca^{2+}]_i$ transients in the absence of extracellular $Ca^{2+}$ (FIG. 3 A-D), indicating that TCR crosslinking with PHA mobilizes $Ca^{2+}$ from the IP$_3$— but not Ry-sensitive store.

When $Ca^{2+}$ was readded following TCR stimulation to allow SOCE, the amplitudes of $[Ca^{2+}]_i$ transients were significantly lower in Ry-pretreated cells than those in the untreated cells (FIG. 3 B, E). On average, preincubation with Ry reduced the maximal amplitudes of $[Ca^{2+}]_i$ transients during $Ca^{2+}$ readdition by 42% (FIG. 3 E), indicating that at physiological conditions $Ca^{2+}$ release from RyR is activated by extracellular $Ca^{2+}$ influx and contributes significantly to $[Ca^{2+}]_i$ elevation.

Inhibition of RyR Downregulates $[Ca^{2+}]_i$ Signaling in Activated But not Resting Human T Lymphocytes.

Consistent with upregulated expression of hRyR1 and hRyR2 genes in activated human T cells, the RyR agonist caffeine produced $Ca^{2+}$ liberation from the ryanodine-sensitive store in the activated human T cells but not in the resting (FIG. 1 C).

Figure 4:
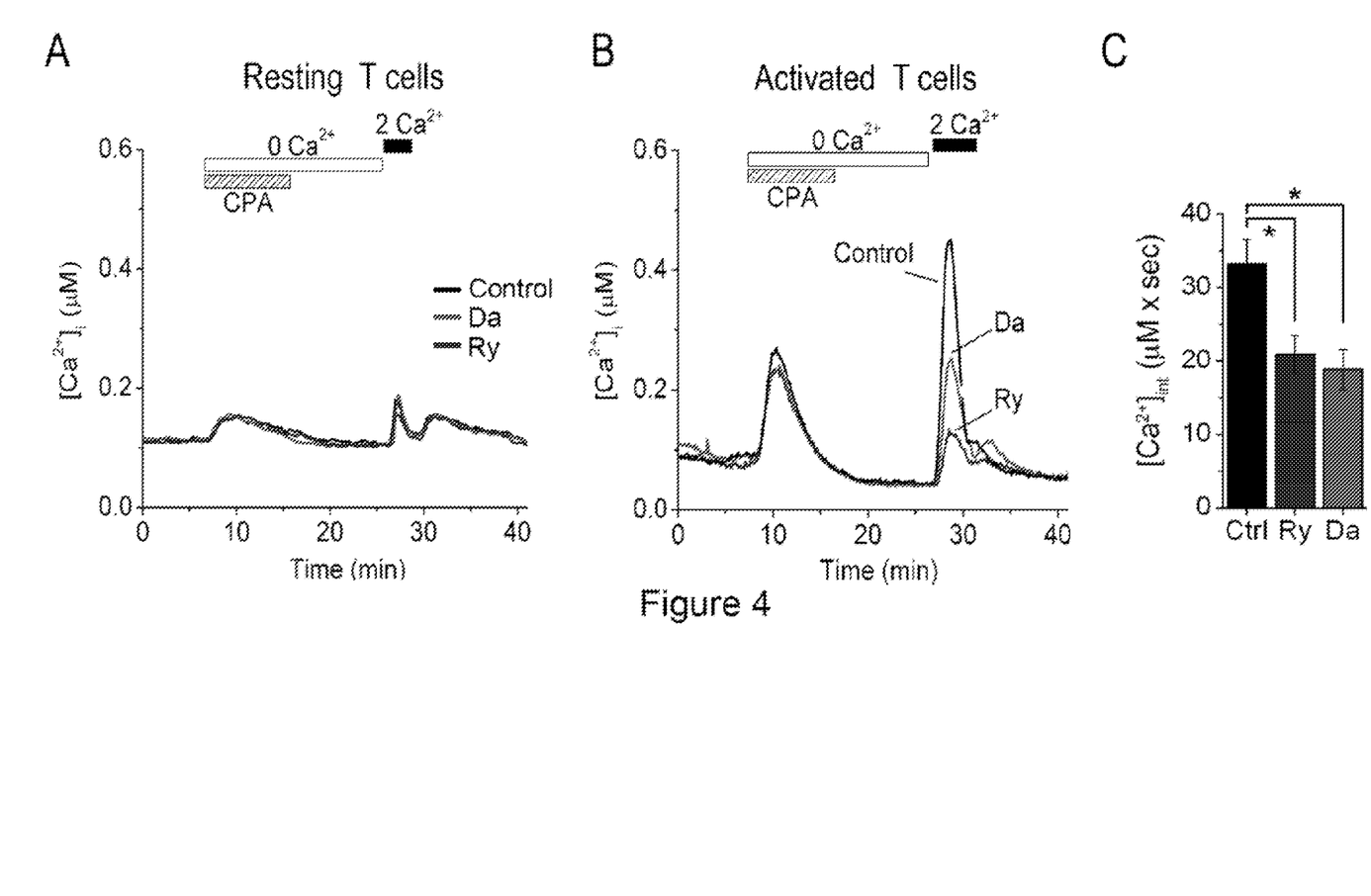

Stimulation with CPA in $Ca^{2+}$-free extracellular solution evoked transient elevation in $[Ca^{2+}]_i$ due to $Ca^{2+}$ release from the intracellular store in both resting and activated human T cells (FIG. 4 A, B). A second $[Ca^{2+}]_i$ transient was evoked by readdition of extracellular $Ca^{2+}$. The average values of integrated $[Ca^{2+}]_i$ transients evoked by $Ca^{2+}$ readdition following store depletion were 15.2±3.4 µM×sec (n=7) in resting T lymphocytes and 33.2±3.3 µM×sec (n=7) in activated T cells.

Furthermore, preincubation of the resting T cells with 30 µM dantrolene (Da), an inhibitor of RyR1 and RyR3 (Zhao, F., Li, P., Chen, S. R., Louis, C. F., and Fruen, B. R. (2001) J Biol Chem 276(17), 13810-13816; Krause, T., Gerbershagen, M. U., Fiege, M., Weisshorn, R., and Wappler, F. (2004) Anaesthesia 59(4), 364-373), or blocking concentrations of Ry (500 µM) did not affect the time courses of changes in $[Ca^{2+}]_i$ (FIG. 4 A), indicating that contribution of Ry-sensitive $Ca^{2+}$ store into global $[Ca^{2+}]_i$ signaling in resting T cells is not essential. In contrast, in activated T cells, both Ry and Da reduced $[Ca^{2+}]_i$ elevation evoked by readdition of extracellular $Ca^{2+}$ (FIG. 4B, C). Thus, overexpression of RyR1 mRNA in activated human T cells correlates with increased contribution of RyR-sensitive store into $Ca^{2+}$ signaling in activated T cells compared with resting, indicating that RyR1 play a significant role in regulation of $Ca^{2+}$ signaling in activated but not resting human T cells and, therefore, may be used as a target for regulation of $Ca^{2+}$-dependent functions of activated human T cells.

Example 3

RyR Blockers Ryanodine and Dantrolene Suppress $Ca^{2+}$-Dependent T Cell Functions Experimental Procedures Cell cultures and chemicals were as described in the Example 1. Proliferation assay—Cell division track assay was conducted using carboxyfluorescein succinimidyl ester (CFSE) proliferation kit (Molecular probes). Stock solution of CFSE (4 mM) was prepared in DMSO. Cells were washed, resuspended in PBS containing 4 µM CFSE at density 1×10$^6$ cells/ml, and incubated at 37° C. for 10 min. Labeling was quenched by adding 5× volume of RPMI 1640 culture media containing 10% FBS. After washing 3 times with RPMI 1640+10% FBS, cells were placed into FBS-free cell culture media to abolish cell division and kept overnight in 5% CO$_2$ at 37° C. After overnight incubation, the CFSE-labeled cells were pellet down and fraction of them (~50000) were fixed with 1% paraformaldehyde in PBS and analyzed by flow cytometry to establish the CFSE fluorescence profile of undivided cells. The remaining CFSE-labeled cells were resuspended in cell culture media supplemented with 10% FBS at density 0.05×10$^6$ cells/ml and seeded into 24 well tissue culture plate (1 ml per well). Some cells were pre-incubated for 30 min at 37° C. with Ry (400 µM), or dantrolene (30 µM) prior to transfer into FBS-containing cell culture media. Drugs were also added to the same cells on each consecutive day of culturing. The vehicles-containing solutions (methanol or DMSO) were applied in place of the drugs in all control experiments. After 72 h in culture, cells were harvested, washed with PBS, and fixed with 1% paraphormaldehyde in PBS. Fluorescence intensity was measured at 488 nm using FACScan flow cytometer and CellQuest software (Becton Dickinson Bioscience, Mountain View, Calif.). The number of cell divisions was calculated using FlowJo software (Tree Star Inc, Ashland, Oreg.).

IL-2 Production Assay—

Jurkat T cells were washed 3 timed with PBS and resuspended in FBS-free cell culture media at density 0.8×10$^6$ cells/ml and seeded into 96 well tissue culture plate (0.4 ml per well) and then stimulated with 100 µM mitogenic lectin phytohaemagglutinin P (PHA). Some cells were pre-incubated for 30 min at 37° C. with, Ry (400 µM), or dantrolene (30 µM) prior to stimulation with PHA. After 24 hours of incubation, cells culture supernatants were collected and contents of IL-2 was determined by ELISA using Quantikine kits (R&D systems, Minneapolis, Minn.) according to manufacturer instructions.

Data Analysis—

Statistical analysis were performed using Origin 7 software (OriginLab, Northampton, Mass.). All data are presented as the mean±standard error of the mean; n=number of experiments. Statistical differences between means were accepted as statistically significant at p<0.05, using Student's paired or unpaired t test or Wilcoxon nonparametric test.
Results CFSE, a fluorescent dye that can be readily loaded into the cytoplasm and then equally distributed between cells after each cell division, resulting in a progressive decrease in CFSE fluorescence in cells that have undergone multiple rounds of divisions (Wells, A. D., Gudmundsdottir, H., and Turka, L. A. (1997) *J Clin Invest* 100(12), 3173-3183). Because Jurkat T cells proliferate instantly without stimulation, the CFSE-labeled Jurkat T cells were first incubated in FBS-free medium to inhibit cell divisions. The proliferation was then induced by transferring cells into complete cell culture media. Resting human $CD3^+$ T cells were isolated from PBMC of healthy volunteers, then labeled with CFSE, and then were activated in vitro with anti-CD3/CD28 Ab to induce proliferation.

Figure 5:
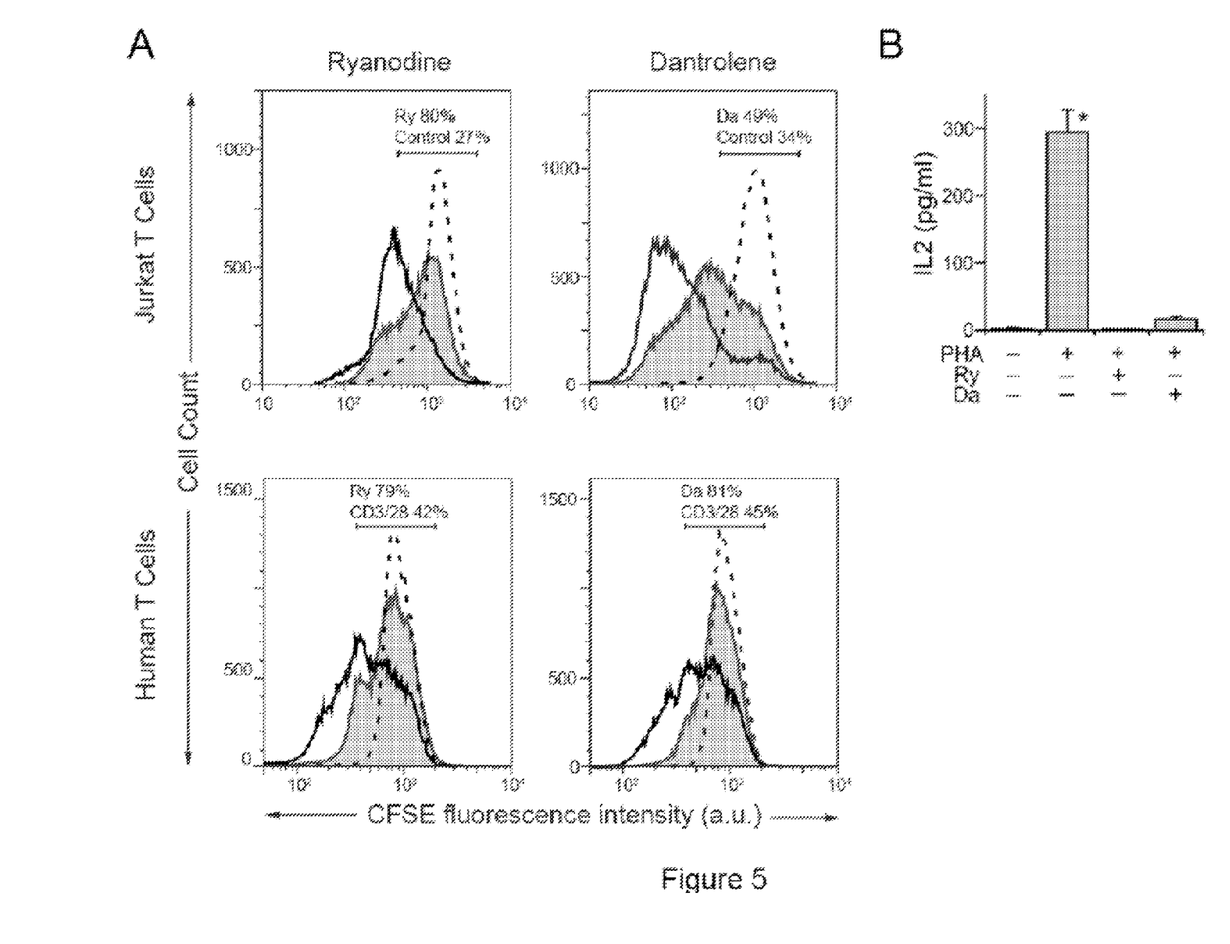

Freshly isolated $CD3^+$ resting human T cells or Jurkat T cells were loaded with CFSE and fraction of them was fixed with 1% paraformaldehyde in PBS and analyzed by flow cytometry to establish the CFSE fluorescence profile of undivided cells (time 0). The remaining CFSE-labeled cells were resuspended in cell culture medium and activated with anti-CD3/CD28 antibodies (human T cells) or transferred into FBS-containing meium (Jurkat T cells). Some cells were pre-incubated for 30 min at 37° C. with ryanodine (Ry, 400 µM) or dantrolene (Da, 30 µM) prior to activation. Drugs were also added to the same cells on each consecutive day of culturing. The vehicle-containing solutions (methanol or DMSO) were applied in place of the drugs to control cells. After 73 h (Jurkat T cells) or 96 h (human T cells) of activation, cells were harvested, fixed, and CFSE fluorescence profiles were determined at 488 nm using FACScan flow cytometer and CellQuest software (Becton Dickinson Bioscience, Mountain View, Calif.). We found that RyR inhibitors significantly (p<0.05, Wilcoxon directional test, n=3 for each condition) reduced proliferation activity of Jurkat human T cells (FIG. 5A). The peaks of CFSE fluorescence profiles obtained from the cells exposed to RyR inhibitors were shifted to the right indicating slower cell cycle progression.

Figure 6:
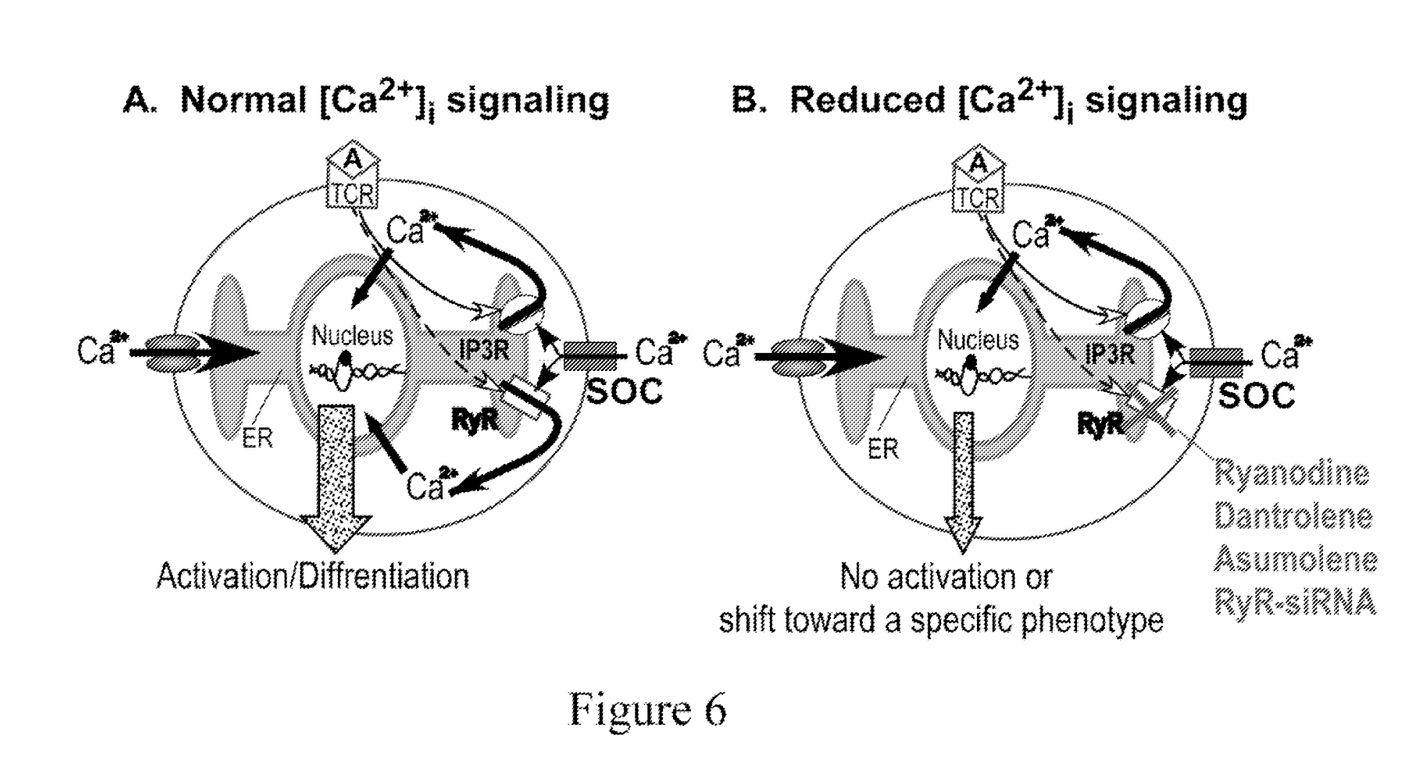

Preincubation with Ry, or Da significantly inhibited PHA-induced IL-2 production (FIG. 5B), which was determined by ELISA. These data indicate that RyR inhibitors are potent modulators of human T cell proliferation and TCR-mediated IL-2 production. The proposed mechanism of action of RyR inhibitors on T cell functions is summarized in FIG. 6.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating or preventing the progression of multiple sclerosis in a patient, the method comprising administering to the patient in need thereof a pharmaceutical composition comprising dantrolene, a dantrolene analogue, or a pharmaceutically acceptable salt thereof and a pharmaceutically acceptable carrier, in the amount and form that is effective to treat or prevent the progression of the disease or disorder, wherein the patient is not suffering from debilitating spasticity.

2. The method of claim 1, wherein the patient is a human.

3. The method of claim 1, wherein the patient is diagnosed with the relapsing-remitting or primary progressive clinically definite-multiple sclerosis or presents a first clinical demyelinating event and multiple sclerosis is highly suspected.

4. The method of claim 1, wherein the dantrolene analogue is azumolene, an azumolene analogue, or a pharmaceutically acceptable salt thereof.

5. The method of claim 1, wherein the pharmaceutically acceptable salt is a sodium salt.

6. The method of claim 1, wherein the pharmaceutically acceptable salt is a quaternary ammonium salt.

7. The method of claim 1, wherein the method further comprises administering the pharmaceutical composition immediately after a first clinical demyelinating event.

8. The method of claim 1, wherein the patient has clinically isolated syndrome (CIS).

9. A method of treating or preventing the progression of a T cell-mediated disorder in a patient selected from the group consisting of graft-versus-host disease and rheumatoid arthritis, the method comprising administering to the patient in need thereof a pharmaceutical composition comprising dantrolene, a dantrolene analogue, or a pharmaceutically acceptable salt thereof and a pharmaceutically acceptable carrier, in the amount and form that is effective to treat or prevent the progression of the disease or disorder.

10. The method of claim 9, wherein the disease is graft versus host disease.

11. The method of claim 9, wherein the disease is rheumatoid arthritis.

12. The method of claim 9, wherein the patient is a human.

13. The method of claim 9, wherein the dantrolene analogue is azumolene, an azumolene analogue, or a pharmaceutically acceptable salt thereof.

14. The method of claim 9, wherein the pharmaceutically acceptable salt is a sodium salt.

15. The method of claim 9, wherein the pharmaceutically acceptable salt is a quaternary ammonium salt.

* * * * *